United States Patent
Kitagawa

(10) Patent No.: US 6,726,633 B2
(45) Date of Patent: Apr. 27, 2004

(54) ADVERTISING METHOD USING AUTOMATIC BLOOD PRESSURE MEASURING APPARATUS, AND AUTOMATIC BLOOD PRESSURE MEASURING APPARATUS HAVING ADVERTISING FUNCTION

(75) Inventor: Hiroya Kitagawa, Komaki (JP)

(73) Assignee: Colin Corporation, Komaki (JP)

( * ) Notice: Subject to any disclaimer, the term of this patent is extended or adjusted under 35 U.S.C. 154(b) by 230 days.

(21) Appl. No.: 09/879,897

(22) Filed: Jun. 14, 2001

(65) Prior Publication Data
US 2002/0002341 A1 Jan. 3, 2002

(30) Foreign Application Priority Data
Sep. 29, 2000 (JP) .......................... 2000-298963

(51) Int. Cl.⁷ .............................. A61B 5/02; G06F 17/60
(52) U.S. Cl. ......................... 600/499; 600/490; 705/1; 705/14; 709/224
(58) Field of Search ................................. 600/301, 485, 600/490, 493, 499, 483, 494; 705/14, 1; 709/203, 217, 224, 232

(56) References Cited

U.S. PATENT DOCUMENTS

| | | | | |
|---|---|---|---|---|
| 4,617,937 A | * | 10/1986 | Peel et al. ................... | 600/493 |
| 4,998,534 A | * | 3/1991 | Claxton et al. .............. | 600/494 |
| 5,913,040 A | * | 6/1999 | Rakavy et al. .............. | 709/232 |
| 6,042,519 A | * | 3/2000 | Shea ........................... | 482/57 |
| 6,317,789 B1 | * | 11/2001 | Rakavy et al. .............. | 709/224 |
| 2002/0010775 A1 | * | 1/2002 | Rakavy et al. .............. | 709/224 |
| 2003/0083929 A1 | * | 5/2003 | Springer et al. ............. | 705/14 |

* cited by examiner

Primary Examiner—Willis R. Wolfe
(74) Attorney, Agent, or Firm—Oliff & Berridge, PLC

(57) ABSTRACT

An advertising method, including the step of displaying, during a blood-pressure measuring operation of an automatic blood-pressure measuring apparatus including an inflatable cuff and a display device, an advertisement on the display device.

3 Claims, 9 Drawing Sheets

| ADVERTISEMENT DATA | ADVERTISEMENT | ADVERTISING CONDITION |
|---|---|---|
| 1 | ADVERTISEMENT A | DENTAL CLINICS |
| 2 | ADVERTISEMENT B | OBSTETRIC CLINICS |
| 3 | ADVERTISEMENT C | CITY HALLS |
| ⋮ | ⋮ | ⋮ |

| | |
|---|---|
| APPARATUS 12 | 300 TIMES |
| APPARATUS 14 | 50 TIMES |
| APPARATUS 16 | 124 TIMES |
| APPARATUS 18 | 16 TIMES |

| APPARATUS | FACILITIES | APPARATUS IDENTIFICATION CODE |
|---|---|---|
| APPARATUS 12 | DENTAL CLINIC | ............ |
| APPARATUS 14 | DENTAL CLINIC | ............ |
| APPARATUS 16 | OBSTETRIC CLINIC | ............ |
| APPARATUS 18 | CITY HALL | ............ |

| RELATIONSHIP | |
|---|---|
| APPARATUS 12 | ADVERTISEMENT A |
| APPARATUS 14 | ADVERTISEMENT A |
| APPARATUS 16 | ADVERTISEMENT B |
| APPARATUS 18 | ADVERTISEMENT C |

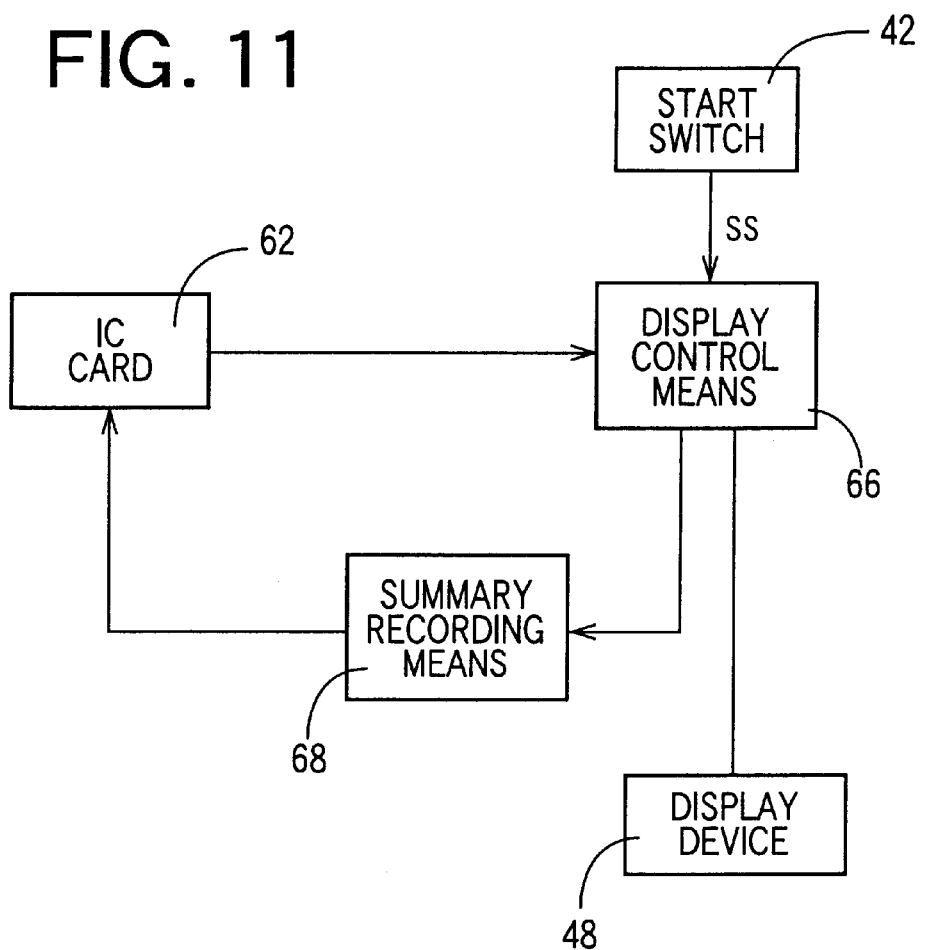

ADVERTISING METHOD USING AUTOMATIC BLOOD PRESSURE MEASURING APPARATUS, AND AUTOMATIC BLOOD PRESSURE MEASURING APPARATUS HAVING ADVERTISING FUNCTION

BACKGROUND OF THE INVENTION

1. Field of the Invention

The present invention relates to an advertising method using an automatic blood-pressure measuring apparatus including an inflatable cuff, and an automatic blood-pressure measuring apparatus having the function of displaying an advertisement during a blood-pressure measuring operation.

2. Related Art Statement

An automatic blood-pressure (BP) measuring apparatus including an inflatable cuff automatically carries out a BP measuring operation by continuously obtaining a physical single from a living subject while a pressing pressure of the cuff wound around a body portion (e.g., upper arm) of the subject is gradually lowered, and determining a BP value or values of the subject based on the obtained signal. The time needed to complete the BP measuring operation, i.e., the time duration in which the cuff presses the body portion of the subject ranges from about 30 seconds to about 1 minute.

As described above, the automatic BP measuring apparatus including the cuff needs 30 seconds to 1 minute to carry out the BP measuring operation. During the BP measuring operation, the subject is bound to the cuff and accordingly cannot do anything.

SUMMARY OF THE INVENTION

It is therefore an object of the present invention to provide the art of effectively utilizing the time in which the BP measuring operation is carried out.

The above object has been achieved by the present invention. According to a first feature of the present invention, there is provided an advertising method, comprising the step of displaying, during a blood-pressure measuring operation of an automatic blood-pressure measuring apparatus including an inflatable cuff and a display device, an advertisement on the display device.

According to the present advertising method, the advertisement is displayed on the display device of the automatic BP measuring apparatus during the BP measuring operation. Since during the BP measuring operation the living subject is bound to the cuff and is likely to see the advertisement displayed on the display device, a high advertising effect is expected and accordingly the time needed to carry out the BP measuring operation is effectively utilized.

According to a second feature of the present invention, there is provided an advertising method, comprising the steps of transmitting, from a host computer which stores an advertisement data base comprising a plurality of advertisements, each one of the advertisements, to at least one of a plurality of automatic blood-pressure measuring apparatuses each of which includes an inflatable cuff and a display device and is connected to the host computer via a communication line, according to a predetermined relationship between the advertisements and the automatic blood-pressure measuring apparatuses, and displaying, during a blood-pressure measuring operation of the one automatic blood-pressure measuring apparatus which has received the each one advertisement, the each one advertisement on the display device of the one automatic blood-pressure measuring apparatus.

According to this advertising method, at the advertisement displaying step, the advertisement is displayed on the display device during the BP measuring operation. Since during the BP measuring operation the living subject is bound to the cuff and is likely to see the advertisement displayed on the display device, a high advertising effect is expected and accordingly the time needed to carry out the BP measuring operation is effectively utilized. In addition, each advertisement is selected, at the advertisement transmitting step, from the plurality of advertisements included in the advertisement data base stored in the host computer, according to the predetermined relationship between the advertisements and the automatic BP measuring apparatuses, and the selected advertisement is transmitted to one or more corresponding automatic BP measuring apparatuses. Thus, each advertisement is displayed by one or more appropriate apparatuses only.

Preferably, the advertising method according to the second feature further comprises the step of transmitting a summary comprising a number of times of displaying of the each one advertisement by the one automatic blood-pressure measuring apparatus, to a terminal of a client who transmitted the each one advertisement to the host computer so that the host computer stores the advertisement data base comprising the each one advertisement.

In this method, the advertising client can know, from the summary transmitted to his or her terminal, how many times his or her advertisement has been displayed by the one automatic BP measuring apparatus.

Preferably, the advertising method according to the second feature further comprises the step of determining the relationship based on an advertising condition which is transmitted, together with the each one advertisement, from the terminal of the client to the host computer.

In this method, the advertising client can more easily cause only one or more appropriate BP measuring apparatuses to display his or her advertisement, as compared with a different method in which the client directly transits his or her advertisement to one or more appropriate BP measuring apparatuses.

According to a third feature of the present invention, there is provided an automatic blood-pressure measuring apparatus, comprising an inflatable cuff which is adapted to be worn on a body portion of a living subject to press the body portion; a display device; at least one advertisement recording medium on which at least one advertisement is recorded; and a display control device which controls the display device to display the advertisement recorded on the advertisement recording medium, during at least a portion of a time period in which a pressing pressure of the cuff applied to the body portion of the subject is changed.

According to this apparatus, the display control device controls the display device to display the advertisement recorded on the advertisement recording medium, during the period in which the pressing pressure of the cuff is changed. Therefore, a high advertising effect is expected and the time needed to carry out the BP measuring operation is effectively utilized.

Preferably, the automatic BP measuring apparatus comprises a plurality of advertisement recording mediums on which a plurality of different advertisements are recorded, respectively, and a first one of the advertisement recording mediums is replaceable with a second one of the advertisement recording mediums.

In this apparatus, the current advertisement displayed on the display device can be easily changed to a different advertisement, by replacing the current advertisement recording medium with another advertisement recording medium on which the different advertisement is recorded.

Preferably, the automatic BP measuring apparatus further comprises a summary recording medium on which a summary comprising a number of times of displaying of the advertisement by the display device is recorded.

In this apparatus, the number of times of displaying of the advertisement can be easily known by reading out the summary recorded on the summary recording medium.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which:

FIG. 3 is a view for explaining an advertisement data base which is stored in a memory device of a host computer as an element of the advertising system of FIG. 1;

FIG. 4 is a view for explaining a summary data base which is stored in the memory device of the host computer;

FIG. 5 is a view for explaining an apparatus data base which is stored in the memory device of the host computer;

FIG. 11 is a block diagram for explaining essential functions of a control device of the automatic BP measuring apparatus of FIG. 10.

DETAILED DESCRIPTION OF PREFERRED EMBODIMENTS

Figure 1:
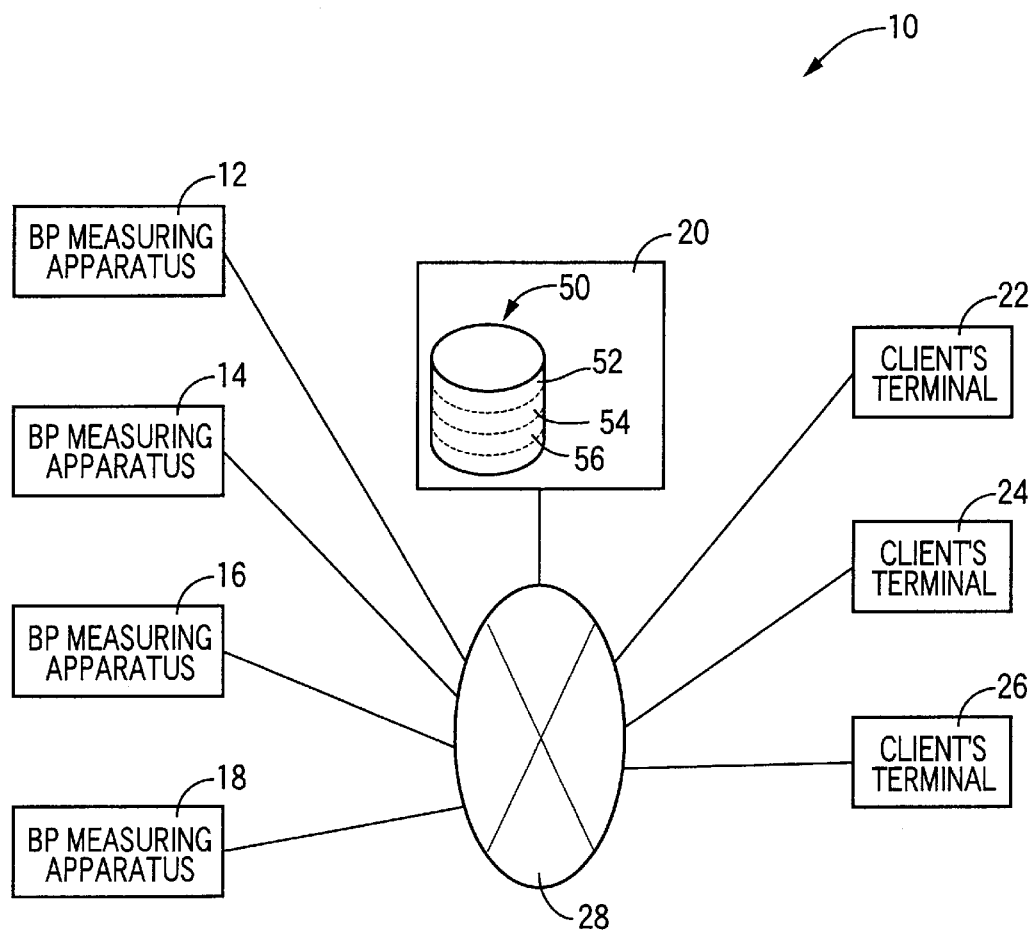
FIG. 1 is a diagrammatic view for explaining a construction of an advertising system which carries out an advertising method to which the present invention is applied.

Hereinafter, there will be described an embodiment of the present invention in detail by reference to the accompanying drawings. FIG. 1 shows a diagrammatic view for explaining a general construction of an advertising system 10 which carries out an advertising method to which the present invention is applied.

In FIG. 1, the advertising system 10 includes a plurality of (e.g., four) automatic blood-pressure (BP) measuring apparatuses 12, 14, 16, 18, a host computer 20, and respective terminals (e.g., personal computers) 22, 24, 26 of a plurality of (e.g., three) advertisement clients, all of which are connected to one another via a communication network 28.

Each of the automatic BP measuring apparatuses 12, 14, 16, 18 includes a microcomputer which automatically measures, according to a prescribed measurement procedure, one or more BP values of a living subject. Each BP measuring apparatus 12, 14, 16, 18 may be placed in a waiting room of a clinic or a hospital, sporting facilities, a pharmacy, a city hall, or a health center. For example, each BP measuring apparatus 12, 14, 16, 18 has an external construction as shown in FIG. 2.

Figure 2:
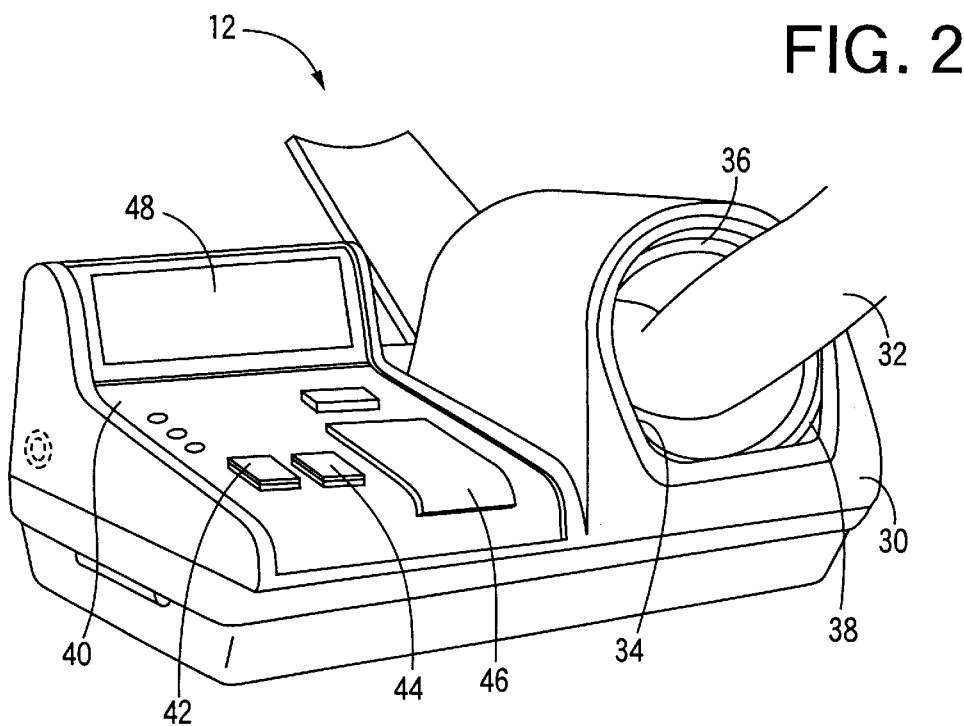
FIG. 2 is a perspective view of one of a plurality of automatic blood-pressure (BP) measuring apparatuses each as an element of the advertising system of FIG. 1.

In FIG. 2, the automatic BP measuring apparatus 12 as a representative of the four apparatuses 12, 14, 16, 18 includes a box 30 having a through-hole 34 through which an arm 32 of the subject is inserted. In the through-hole 34, there is provided an outer belt 38 which is flexible but considerably hard and which takes a generally cylindrical shape. An inflatable cuff 36 is supported by an inner surface of the cylindrical outer belt 38. The box 30 additionally has an operation panel 40 including a start switch 42, a stop switch 44, and a printer 46. Moreover, the box 30 has a display device 48 which is contiguous to the operation panel 40 and which faces the subject so as to be easily observed by the same. The display device 48 displays not only measured BP values and pulse rate, and a time of measurement of the BP values and pulse rate, but also an advertisement. For example, the display device 48 is provided by a dot-matrix-type color liquid crystal display panel or a plasma display panel (PDP) which has a considerably large size and which can display characters, figures, and symbols. However, the display device 48 may be one which can display characters only, or one which can display characters and images. The BP measuring apparatus 12 further includes a memory device and a signal transmitting and receiving device, not shown.

When the start switch 42 of the automatic BP measuring apparatus 12 is operated in a state in which the arm 32 of the subject is inserted through the through-hole 34 of the box 30, the apparatus 12 automatically measures one or more BP values of the subject. More specifically described, when the start switch 42 is operated, the belt 38 and the cuff 36 are wound up around the arm 32, and the pressing pressure of the cuff 36 is first quickly increased to a prescribed target pressure value (e.g., 180 mnHg) and is then slowly decreased at a prescribed low rate (e.g., 3 mmHg/sec). Based on the pressure signal obtained from the cuff 36 during the slow deflation of the cuff 36, one or more BP values of the subject are determined by the microcomputer according to a well-known oscillometric BP determining algorithm. The thus determined BP values are displayed on the display device 48, and are printed on a recording medium (e.g., paper) by the printer 46.

Back to FIG. 1, the host computer 20 includes a memory device 50. The memory device 50 may be provided by a random access memory (RAM), a magnetic-disc device (HDD), or a removable medium (e.g., MO or DVD). The memory device 50 stores, in respective prescribed memory areas thereof, an advertisement data base 52, a summary data base 54, and an apparatus data base 56.

The advertisement data base 52 includes respective sets of advertisement data which are transmitted from the clients' terminals 22, 24, 26. Each set of advertisement data includes an advertisement, and an advertising condition associated with the advertisement. The advertising condition designates one or more facilities, so that the advertisement is displayed by only one or more automatic BP measuring apparatuses placed in the designated facilities. FIG. 3 shows the advertisement data base 52 stored in the memory device 50. For example, an advertisement, A, relates to a toothpaste, and an advertising condition associated with the advertisement A designates dental clinics only, so that the advertisement A is displayed by only one or more automatic BP measuring apparatuses placed in the dental clinic or clinics.

The summary data base 54 includes respective sets of summary data which are transmitted from the automatic BP measuring apparatuses 12, 14, 16, 18. Each set of summary data includes the total number of times of displaying of each advertisement by each automatic EC measuring apparatus, and/or the frequency of displaying of each advertisement (per day, week, month, etc.) by each automatic EC measuring apparatus; an apparatus identification code (e.g., sequential number) which identifies the each automatic EC measuring apparatus; and an advertisement identification code which identifies the each advertisement. FIG. 4 shows the summary data base 54 stored in the memory device 50. However, the frequency of displaying of the each advertisement, or the advertisement identification code identifying the each advertisement is not shown in FIG. 4. FIG. 5 shows the apparatus data base 56 which includes, for the automatic EC measuring apparatuses 12, 14, 16, 18, the respective apparatus identification codes which identify the apparatuses 12, 14, 16, 18, and the respective facilities in which the apparatuses 12, 14, 16, 18 are placed.

Each of the respective terminals 22, 24, 26 of the advertising clients includes an input device, not shown, through which a set of advertisement data is input, and transmits the input set of advertisement data to the host computer 20. When a new set of advertisement data is transmitted from each client's terminal 22, 24, 26 to the host computer 20, the old set of advertisement data is replaced with the new set of advertisement data in the advertisement data base 52 of the memory device 50. Thus, each client can easily change or update an advertisement itself and/or an advertising condition associated with the advertisement.

The communication network 28 may be constituted by communication lines, such as public telephone lines (e.g., ISDN lines), a wired or wireless local area network (LAN) (the wired LAN may be constituted by optical fibers), a satellite communication line, or cable-television (CATV) lines.

Figures 6, 7:
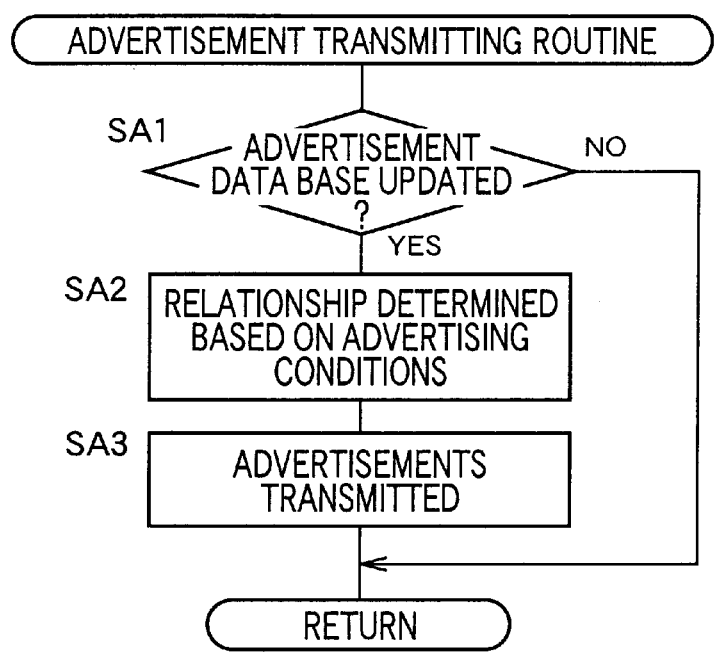
FIG. 6 is a flow chart representing an advertisement transmitting routine according to which the host computer transmits an advertisement to one or more appropriate automatic BP measuring apparatuses.
FIG. 7 is a view for explaining a relationship which is determined according to the advertisement transmitting routine of FIG. 6.

FIG. 6 is a flow chart representing an advertisement transmitting routine according to which the host computer 20 transmits each advertisement to one or more appropriate automatic BP measuring apparatuses. The advertisement transmitting routine is a control program which is stored in a read only memory (ROM; not shown) of the computer 20. First, at Step SA1 (hereinafter, "Step" is omitted), the computer 20 judges whether the advertisement data base 52 has been changed or updated. If a negative judgment is made at SA1, the current control cycle according to this routine is terminated. On the other hand, if one of the clients' terminals 22, 24, 26 has transmitted a new set of advertisement data to the host computer 20 and the old set of advertisement data is replaced with the new set of advertisement data in the advertisement data base 52, a positive judgment is made at SA1. Then, the control of the computer 20 goes to SA2 as a relationship determining step. More specifically described, at SA2, the computer 20 determines, based on the advertising conditions included in the sets of advertisement data included in the updated advertisement data base 52, and the facilities included in the apparatus data base 56 associated with the automatic BP measuring apparatuses 12, 14, 16, 18, a relationship between the advertisements A, B, C, and the apparatuses 12, 14, 16, 18, as shown in FIG. 7.

Next, at SA3 as an advertisement transmitting step, the computer 20 transmits, according to the relationship determined at SA2, each of the three advertisements A, B, C included in the advertisement data base 52, to one or more appropriate apparatuses of the four automatic BP measuring apparatuses 12, 14, 16, 18. Thus, each advertisement is transmitted to, and stored by, only one or more automatic BP measuring apparatuses placed in one or more facilities in which each client wishes to display the each advertisement.

Figure 8:
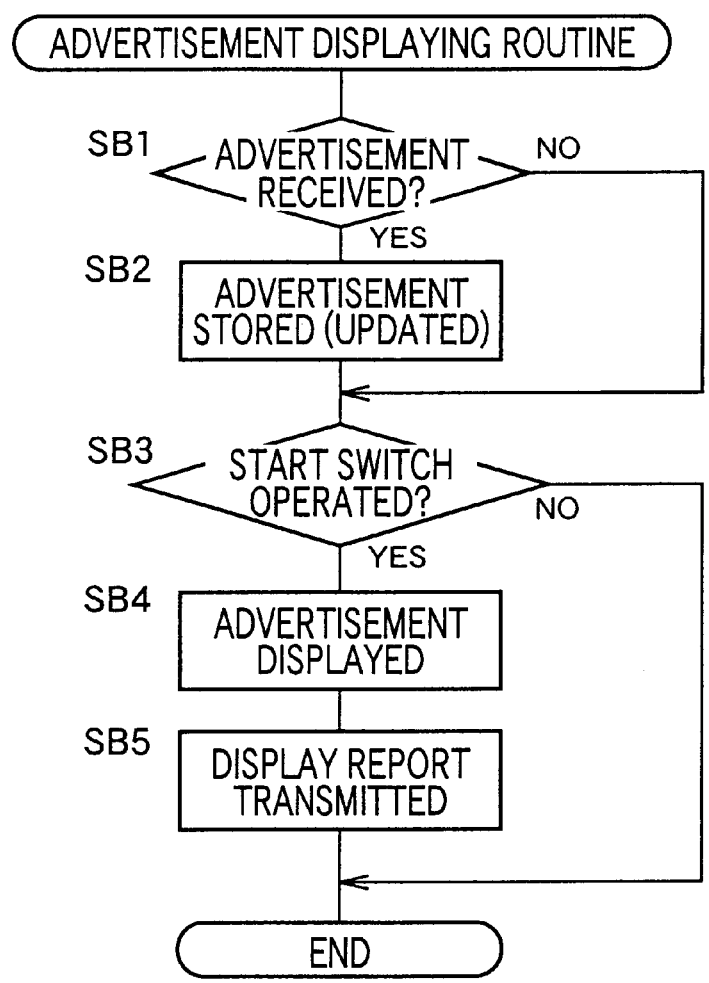
FIG. 8 is a flow chart representing an advertisement displaying routine according to which each automatic BP measuring apparatus displays an advertisement.

FIG. 8 is a flow chart representing an advertisement displaying routine according to which each of the automatic BP measuring apparatuses 12, 14, 16, 18 displays the advertisement transmitted thereto from the host computer 20. The advertisement displaying routine is a control program which is stored in a ROM (not shown) of the microcomputer of each apparatus 12, 14, 16, 18. First, at SB1, the microcomputer of each apparatus 12, 14, 16, 18 judges whether an advertisement has been transmitted thereto from the host computer 20. More specifically described, the microcomputer judges whether the signal transmitting and receiving device (not shown) of the each apparatus 12, 14, 16, 18 has received an advertisement which is transmitted thereto from the host computer 20 either directly, or indirectly via a server. If a negative judgment is made at SB1, the control of the microcomputer skips SB2 and goes directly to SB3 and the following step. On the other hand, if a positive judgment is made at SB1, the control goes to SB2 where the microcomputer stores the received advertisement in a random access memory (RAM; not shown) thereof.

Next, at SB3, the microcomputer judges whether the start switch 42 has been operated. If a negative judgment is made at SB3, the current control cycle according to this routine is terminated. On the other hand, if a positive judgment is made at SB3, the control goes to SB4 as an advertisement displaying step. At SB4, the microcomputer controls the display device 48 to display the advertisement stored at SB2, during a time duration in which the pressing pressure of the cuff 36 is changed. The advertisement may be displayed during either the entirety, or only a portion, of the BP measuring operation.

Next, at SB5, the microcomputer controls the signal transmitting and receiving device to transmit, to the host computer 20, a display report that the advertisement has been displayed.

Figure 9:
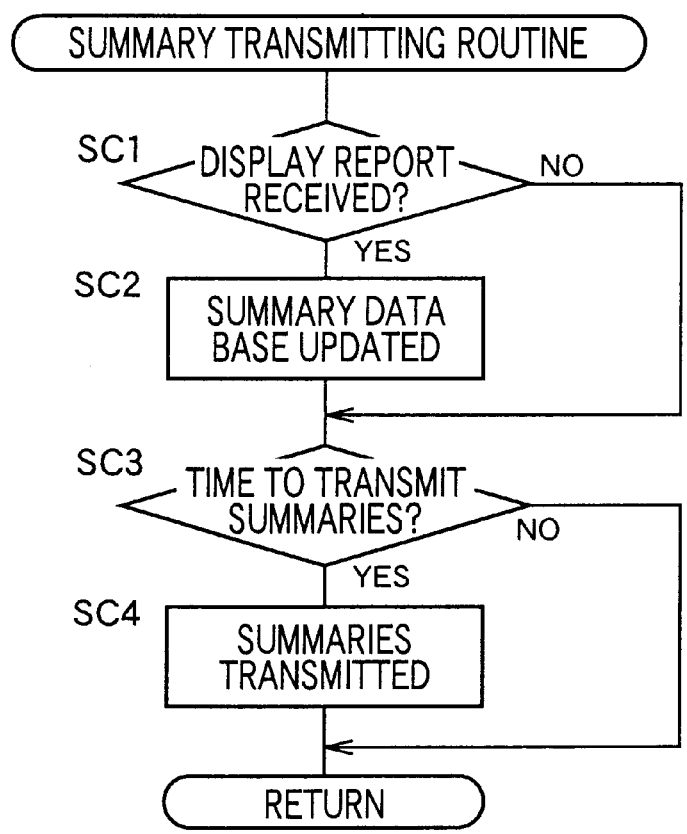
FIG. 9 is a flow chart representing an achievement transmitting routine according to which the host computer transmits an advertisement summary to a terminal of one or more appropriate clients.

FIG. 9 is a flow chart representing a summary transmitting routine according to which the host computer 20 transmits respective sets of summary data to the respective terminals 22, 24, 26 of the advertising clients. The summary transmitting routine is a control program which is stored in the ROM of the computer 20. First, at Step SC1, the computer 20 judges whether the computer 20 has received a display report from any one of the automatic BP measuring apparatuses 12, 14, 16, 18. If a negative judgment is made at SC1, the control of the computer 20 goes directly to SC3 and the following steps.

On the other hand, if a positive judgment is made at SC1, the control goes to SC2 to update the summary data base 54 based on the received display report.

When a negative judgment is made at SC1, or after SC2 is finished, the control goes to SC3 and SC4 corresponding to a summary transmitting step. First, at SC3, the computer 20 judges whether it is a prescribed time to transmit the sets of summary data. The prescribed time may be one in every day, every week, or every month, or whenever an advertisement has been displayed a prescribed number of times.

If a negative judgment is made at SC3, the current control cycle according to this routine is ended. On the other hand, if a positive judgment is made at SC3, the control goes to SC4 to transmit, according to the relationship determined at SA2 of FIG. 6, each of the respective sets of summary data included in the summary data base 54 associated with the automatic BP measuring apparatuses 12, 14, 16, 18, to a corresponding one of the clients' terminals 22, 24, 26. Each of the clients pays, to an owner of the present advertising system 10, an advertising fee based on the set of summary data transmitted from the host computer 20, and/or when the each client transmits a set of advertisement data from his or her terminal to the host computer 20. Owing to those advertising fees, the owner of the advertising system 10 can provide the facilities (e.g., hospitals) with the automatic BP measuring apparatuses 12, 14, 16, 18 at a lower price.

It emerges from the foregoing description that at the advertisement displaying step (SB4), an advertisement is displayed on the display device 48 during a BP measuring operation. Since during the BP measuring operation the living subject is bound to the cuff 36 and is likely to see the advertisement displayed on the display device 48, a high advertising effect is expected and accordingly the time needed to carry out the BP measuring operation is effectively utilized. In addition, since the advertisement displayed on the display device 48 is selected, according to the predetermined relationship, shown in FIG. 7, from the plurality of advertisements included in the advertisement data base 52 stored in the memory device 50 of the host computer 20, and is transmitted at the advertisement transmitting step (SA3), the displayed advertisement is an appropriate one.

In addition, in the present embodiment, at the summary transmitting step (SC3 and SC4), each of the sets of summary data is transmitted to a corresponding one of the respective terminals 22, 24, 26 of the advertising clients. Therefore, each of the clients can know, from the set of summary data transmitted to his or her terminal, how many times his or her advertisement has been displayed.

Moreover, in the present embodiment, at the relationship determining step (SA2), a relationship (FIG. 7) between the plurality of advertisements included in the advertisement data base 52 and the plurality of automatic BP measuring apparatuses 12, 14, 16, 18 is predetermined based on the advertising conditions made by the clients. Therefore, the advertisement of each client can be more easily displayed by only one or more appropriate BP measuring apparatuses, as compared with a manner in which each client directly selects one or more appropriate BP measuring apparatuses and requests the selected apparatus or apparatuses to display his or her advertisement.

Next, there will be described a second embodiment of the present invention. The same reference numerals as used in the first embodiment shown in FIGS. 1 to 9 are also used to designate the corresponding elements or parts of the second embodiment, and the description thereof is omitted.

Figure 10:
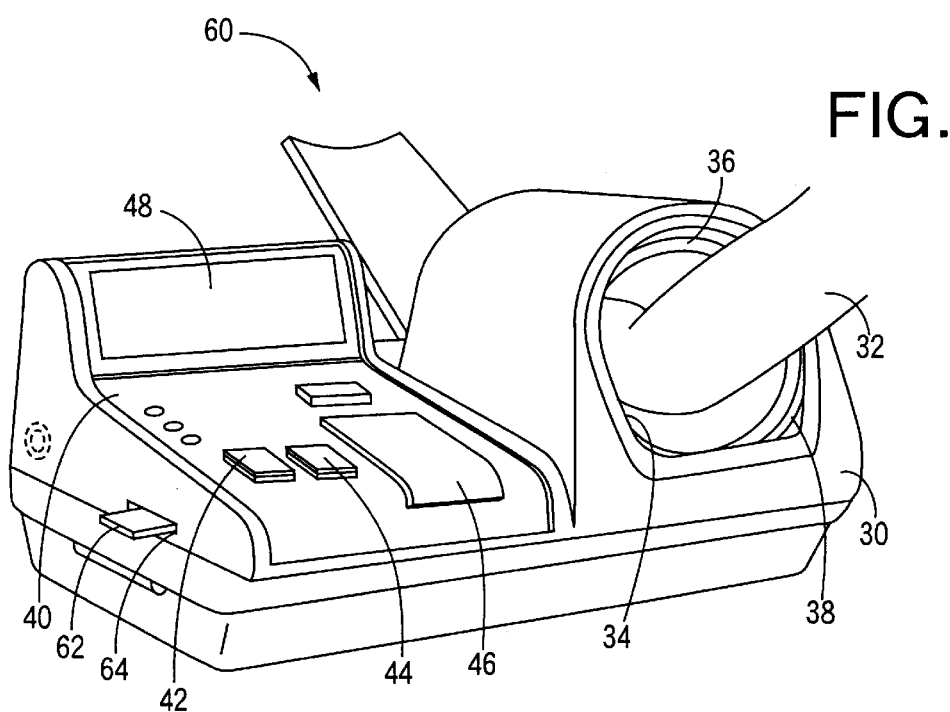
FIG. 10 is a perspective view of an automatic BP measuring apparatus to which the present is also applied.

FIG. 10 is a perspective view showing an external construction of an automatic BP measuring apparatus 60 to which the present invention is applied. Like the above-described automatic BP measuring apparatuses 12, 14, 16, 18, the present automatic BP measuring apparatus 60 is disposed in, e.g., a waiting room of a clinic or a hospital, sporting facilities, a pharmacy, a city hall, or a health center.

However, the automatic BP measuring apparatus 60 shown in FIG. 10 is not connected to the communication network 28 shown in FIG. 1, and therefore the apparatus 60 cannot receive an advertisement via the network 28. In the second embodiment, an advertisement is recorded, in advance, on an integrated circuit (IC) card 62 as an advertisement recording medium.

The IC card 62 stores one or more advertisements which is or are provided by an advertising client. The IC card 62 is inserted into a slot 64 formed in a side surface of the box 30 of the BP measuring apparatus 60, so that the IC card 62 is detachably attached to the apparatus 60. The current IC card 62 can be replaced with another IC card 62 which stores one or more advertisements which is or are provided by another advertising client. The apparatus 60 includes a card reader, not shown, which reads each advertisement recorded on each IC card 62 inserted in the slot 64. Therefore, a manager who manages the IC cards 62, for example, a maintainer who maintains the BP measuring apparatus 60 can easily change the advertisements displayed by the apparatus 60, either periodically or as needed, by replacing the current IC card 62 inserted in the slot 64, with another IC card.

FIG. 11 is a block diagram for explaining essential functions of a control device (e.g., a microcomputer), not shown, of the automatic BP measuring apparatus 60.

As shown in FIG. 11, the control device includes a display control means 66 which also functions as a BP-measurement-period judging means. Based on a start signal, SS, supplied from the start switch 42, the display control means 66 judges whether it is now in a BP-measurement period, that is, in a period in which the pressing pressure of the cuff 36 applied to the arm 32 of the living subject is changed. During the BP-measurement-period, the display control means 66 controls the display device 48 to display the advertisement recorded on the IC card 62. The displaying of the advertisement may be started immediately after the BP measurement period is started, or at the time when a prescribed time has passed after the period is started. The displaying of the advertisement may be ended at the time when the BP measurement period is ended, or a prescribed time before or after the period is ended.

A summary recording means 68 records, on the IC card 62 inserted in the slot 64, a set of summary data representing a summary including a number of times of displaying of each advertisement by the display device 48, and a total time in which each advertisement is displayed by the display device 48. Since the IC card 62 stores the set of summary data, the IC card 62 also functions as a summary recording medium.

The manager who manages the IC cards 62, either periodically or as needed, operates the card reader of the automatic BP measuring apparatus 60 to read the set of summary data recorded on the current IC card 62 inserted in the slot 64, and display an image (e.g., characters and numerals) representing the summary on the display device 48. In addition, the manager reports the summary to the advertising client, as needed.

It emerges from the foregoing description that in the second embodiment shown in FIGS. 10 and 11, the display control means 66 controls the display device 48 to display, during the period in which the pressing pressure of the cuff 36 is changed, the advertisement stored in the IC card 62. Thus, a high advertising effect is expected, and accordingly the time needed to carry out the BP measuring operation is effectively utilized.

In addition, in the second embodiment, the current IC card 62 inserted in the slot 64 of the automatic BP measuring apparatus 60 can be replaced with another IC card 62 which stores the different advertisement from the current advertisement stored in the current IC card 62. Thus, the current advertisement displayed on the display device 48 can be easily changed to a different advertisement.

Moreover, in the second embodiment, the IC card 62 stores the set of summary data including the number of times of displaying of the advertisement stored in the IC card 62. Thus, the number of times of displaying of the advertisement can be easily known by reading out the set of summary data from the IC card 62.

While the present invention has been described in its preferred embodiments by reference to the drawings, it is to be understood that the invention may otherwise be embodied.

For example, in the first embodiment shown in FIGS. 1 to 9, at the relationship determining step (SA2), the relationship between the advertisements and the automatic BP measuring apparatuses 12, 14, 16, 18 is determined based on the advertising conditions made by the advertising clients. However, each client may directly determine a relationship between his or her advertisement and one or more automatic BP measuring apparatuses which he or she wishes to display the advertisement. That is, each client may directly designate one or more automatic BP measuring apparatuses which he or she wishes to display his or her advertisement.

In addition, in the first embodiment, each time the advertisement data base 52 is updated, each of the advertisements included in the data base 52 are transmitted, at SA3, to one or more corresponding automatic BP measuring apparatuses. However, it is possible that only the updated advertisement be transmitted to one or more corresponding automatic BP measuring apparatuses.

Each of the automatic BP measuring apparatuses 12, 14, 16, 18, 60 is an oscillometric-type automatic BP measuring apparatus. However, so long as an automatic BP measuring apparatus employs an inflatable cuff, such as a finger cuff, a wrist cuff, or an arm cuff, the apparatus may determine one or more BP values of a living subject in a different method, such as a Korotkoff-sound method.

In each of the automatic BP measuring apparatuses 12, 14, 16, 18, 60, the display device 48 is supported by the box 30, such that the device 48 is integral with the other portions of the each apparatus. However, the display device 48 may be provided as an element which is separate from the other portions of the each apparatus. For example, a display device may be provided at a position which is expected to face a thorax or a face of a living subject who inserts his or her arm 32 in the hole 34 of the box 30. In short, the display device 48 just needs to be provided at a position where the device 48 faces the subject.

In the second embodiment shown in FIGS. 10 and 11, each IC card 62 functions as not only the advertisement recording medium but also the summary recording medium. However, the advertisement recording medium and the summary recording medium may be separate from each other, i.e., may be provided by two separate recording mediums, respectively. In the latter case, the advertisement recording medium may be provided by a read only recording medium (e.g., ROM).

In addition, in the second embodiment, each IC card 62 which can be detachably attached to the automatic BP measuring apparatus 60 functions as not only the advertisement recording medium but also the summary recording medium. That is, each of the advertisement recording medium and the summary recording medium can be detachably attached to the apparatus 60. However, the advertisement or summary recording medium may be employed in the apparatus 60 such that the medium cannot be detached from the apparatus, e.g., may be incorporated in the apparatus 60. Therefore, the advertisement or summary recording medium may be provided by a RAM or a hard disc. Otherwise, the advertisement or summary recording medium may be provided by a removable medium, such as a floppy disc or an MO.

Moreover, in the second embodiment, the display control means 66 judges, based on the start signal SS supplied from the start switch 42, whether it is now in a BP-measurement-period. However, the display control means 66 may be modified to judge whether it is now in a BP-measurement period, based on a pressure in the cuff 36, or an operation of a pressure control device, not shown, which controls (i.e., increases and decreases) the pressure in the cuff 36.

It is to be understood that the present invention may be embodied with other changes, improvements, and modifications that may occur to a person skilled in the art without departing from the spirit and scope of the invention defined in the appended claims.

What is claimed is:

1. An automatic blood-pressure measuring apparatus, comprising:

an inflatable cuff which is adapted to be worn on a body portion of a living subject to press the body portion;

a display device;

a plurality of advertisement recording media on which at a plurality of different advertisements are recorded respectively, and a first one of the plurality of advertisement recording media is replaceable with a second one of the plurality of advertisement recording media;

a display control device which controls the display device to display the plurality of different advertisements recorded on the plurality of different advertisement recording media, during at least a portion of a time period in which a pressing pressure of the cuff applied to the body portion of the subject is changed; and a summary recording medium on which a summary comprising a number of times of displaying of the plurality of different advertisements by the display device is recorded, wherein said summary is transmitted to a terminal of a client who transmitted said each one of the plurality of different advertisements to a host computer so that the host computer stores an advertisement data base comprising each one of the plurality of different advertisements.

2. An advertising method, comprising:

transmitting, from a host computer which stores an advertisement data base comprising a plurality of advertisements, each one of the advertisements, to at least one of a plurality of automatic blood-pressure measuring apparatuses each of which includes an inflatable cuff and a display device and is connected to the host computer via a communication line, according to a predetermined relationship between the advertisements and the automatic blood-pressure measuring apparatuses;

displaying, during a blood-pressure measuring operation of said one automatic blood-pressure measuring apparatus which has received said each one advertisement, said each one advertisement on the display device of said one automatic blood-pressure measuring apparatus; and transmitting a summary comprising a number of times of displaying of said each one advertisement by said one automatic blood-pressure measuring apparatus, to a terminal of a client who transmitted said each one advertisement to the host computer so that the host computer stores the advertisement data base comprising said each one advertisement.

3. An advertising method according to claim 2, further comprising a step of determining the relationship based on an advertising condition which is transmitted, together with said each one advertisement, from the terminal of the client to the host computer.

* * * * *